United States Patent
Kayane et al.

(10) Patent No.: US 6,428,770 B1
(45) Date of Patent: Aug. 6, 2002

(54) SOLID PREPARATION FOR ORAL HYGIENE

(75) Inventors: Shigeto Kayane; Yoshitaka Yano; Shinji Kiji, all of Tokyo; Keiko Masuki, Ichikai-machi; Hidetake Fujinaka, Tokyo; Yasuteru Eguchi, Ichikai-machi; Mitsuyoshi Kashiwagi, Tokyo, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/554,621

(22) PCT Filed: Dec. 3, 1997

(86) PCT No.: PCT/JP97/04415

§ 371 (c)(1),
(2), (4) Date: Jun. 2, 2000

(87) PCT Pub. No.: WO99/27901

PCT Pub. Date: Jun. 10, 1999

(51) Int. Cl.$^7$ ............................. A61K 7/16; A61K 9/24; A61K 9/46
(52) U.S. Cl. ......................................... 424/44; 424/435
(58) Field of Search .................... 424/44, 49–58

(56) References Cited

U.S. PATENT DOCUMENTS

| | | | | |
|---|---|---|---|---|
| 462,990 A | * | 11/1891 | Oppenhemer | 167/83 |
| 2,769,011 A | * | 10/1956 | Hacker | 260/314 |
| 2,794,762 A | * | 6/1957 | Westcott | 167/55 |
| 2,815,314 A | * | 12/1957 | Hale | 167/65 |
| 2,922,742 A | * | 1/1960 | Scanlon | 424/440 |
| 3,048,526 A | * | 8/1962 | Boswell | 167/82 |
| 3,096,248 A | * | 7/1963 | Rudzki | 167/82 |
| 3,518,343 A | * | 6/1970 | Welsh et al. | 424/44 |
| 3,629,468 A | * | 12/1971 | Andersen | 424/44 |
| 3,772,431 A | * | 11/1973 | Mlkvy et al. | 424/44 |
| 3,888,976 A | * | 6/1975 | Mlkvy et al. | 424/44 |
| 3,962,417 A | * | 6/1976 | Howell | 424/52 |
| 4,198,390 A | * | 4/1980 | Rider | 424/21 |
| 4,503,031 A | * | 3/1985 | Glassman | 424/44 |
| 4,678,661 A | * | 7/1987 | Gergely | 424/44 |
| 4,789,546 A | * | 12/1988 | Medri | 424/441 |
| 4,898,733 A | * | 2/1990 | DePrince et al. | 424/429 |
| 4,915,948 A | * | 4/1990 | Gallopo et al. | 424/435 |
| 4,919,918 A | * | 4/1990 | Cole et al. | 424/44 |
| 4,971,785 A | * | 11/1990 | Wilson et al. | 424/44 |
| 5,415,870 A | * | 5/1995 | Gergely | 424/466 |
| 5,736,158 A | * | 4/1998 | Quast | 424/52 |
| 5,804,165 A | * | 9/1998 | Arnold | 424/44 |
| 5,912,012 A | * | 6/1999 | Carlin et al. | 424/464 |
| 6,086,854 A | * | 7/2000 | Arnold | 424/44 |

FOREIGN PATENT DOCUMENTS

JP  88/10110  12/1988

OTHER PUBLICATIONS

English Language Abstract of JP 61–236718, Oct. 22, 1986.

* cited by examiner

Primary Examiner—Shep K. Rose
(74) Attorney, Agent, or Firm—Oblon, Spivak, McClelland, Maier & Neustadt, P.C.

(57) ABSTRACT

The present invention relates to a solid preparation for oral hygiene, which comprises (a) 15 to 90 wt. % of a bubbling component and (b) 0.001 to 10 wt. % of an orally-usable medicinal component at an (a):(b) ratio ranging from 10:1 to 1000:1. Use of the preparation brings about a drastic improvement in the drug efficacy and moreover, breath is freshened by bubbling.

7 Claims, 1 Drawing Sheet

SOLID PREPARATION FOR ORAL HYGIENE

This application is a 371 of PCT JP97/04415 Dec. 3, 1997.

TECHNICAL FIELD

The present invention relates to a solid preparation for oral hygiene, which conducts oral cleaning by bubbling and in addition, is improved in exhibition of the effects of the medicinal component contained therein.

BACKGROUND ART

Although there has been an attempt to incorporate an orally-usable medicinal component such as halitosis-preventing component in a quasi-drug or a drug in the orally soluble form, such a preparation does not exhibit satisfactory halitosis-preventing effects or the like.

As preparations containing a bubbling component and a medicinal component, an effervescent tablet as described in WO93/00886 and a gargle as described in Japanese Patent Application Laid-Open No. HEI 1-275521 (U.S. Ser. No. 167,504) are known. The former one is, however, a compound exhibiting its drug efficacy when its medicinal component is absorbed from digestive tracts such as intestines. An aqueous solution obtained in advance by dissolving the preparation in water is orally taken. The bubbling component is added to the preparation only for promoting the dissolution of the medicinal component. The latter one is a gargle used in the form of an aqueous solution obtained by dissolving a tablet, thereby dissolving its components in water.

As described above, a preparation which comprises an orally-usable medicinal component and a bubbling component and is caused to bubble and is dissolved inside of the oral cavity with a view to orally releasing the medicinal component, thereby exhibiting its effects, while carrying out breath freshening and cleaning by bubbling is not known at all.

DISCLOSURE OF THE INVENTION

The present inventors have therefore made various investigations on an orally-usable solid preparation which comprises a bubbling component and a medicinal component acting in the oral cavity and is caused to bubble and is dissolved inside of the oral cavity upon use. As a result, it has been found that when a preparation comprising a high-concentration bubbling component and an orally-usable medicinal component at a specific ratio is used, the oral cavity is cleaned, particularly fur coating on the dorsum of tongue is effectively removed, by bubbling in the mouth, and the orally-usable medicinal component acts on the filiform papillae on the dorsum of tongue exposed by the removal, whereby the drug efficacy of the medicinal component shows a synergistic improvement. It has also been found that if the preparation is designed to effect bubbling prior to dissolution of the medicinal component, adhesion efficiency of the medicinal component to the filiform papillae on the dorsum of tongue shows a drastic improvement, thereby sustaining the drug efficacy, leading to the completion of the present invention.

In the present invention, there is thus provided a process for oral hygiene treatment, which comprises taking a solid preparation (which will hereinafter be called "solid preparation of the present invention") containing the following components (a), (b) and (c):

(a) an effervescent component: 15 to 90 wt. %,
(b) an orally-usable medicinal component: 0.001 to 10 wt. %, and
(c) an excipient: not greater than 84.999 wt. % at a weight ratio of (a):(b) ranging from 10:1 to 1000:1 to bring it in contact with water in the mouth, thereby causing bubbling and dissolution of it in the water; and swallowing the resulting aqueous solution or discharging it out of the mouth.

In another aspect of the present invention, there is also provided the above-described process, wherein by controlling the component ratio of (a):(b) in each part of the solid preparation, the bubbling owing to the component (a) is rendered to proceed in the initial stage of dissolution in the mouth and the dissolution of the component (b) is rendered to proceed even after completion of the bubbling.

In a further aspect of the present invention, there is also provided the use of the solid preparation of the present invention for oral hygiene.

In a still further aspect of the present invention, there is also provided a solid preparation for oral hygiene which is dissolved inside of the oral cavity upon use, wherein the component (a) and the component (b) differ in the relative concentration in each part of the preparation, more specifically, the relative concentration of the component (a) is high in the part of the preparation wherein dissolution occurs earlier in the mouth and that of the component (b) is high in the part wherein dissolution occurs later.

BEST MODES FOR CARRYING OUT THE INVENTION

Figure 1:
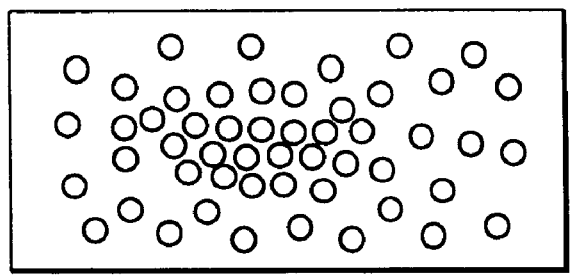
FIG. 1 is a cross-sectional view illustrating the solid preparation (tablet) of the present invention which is designed to contain the component (a) at a high relative concentration in the outer part, while containing the component (b) at a high relative concentration in the inner part, wherein small circles show the component (b)

The solid preparation of the present invention is characterized by that it contains a high-concentration bubbling component (a) and an orally-usable medicinal component (b) at a specific ratio. Such a constitution makes it possible to sufficiently remove the fur coating on the tongue. Moreover, by causing the medicinal component to act on the place from which the fur coating is removed, pharmacological effects available by the preparation are synergistically high.

Here, as the bubbling component (a), carbon-dioxide-gas emitting components containing a carbonate and an organic acid are preferred. Examples of the organic acid include citric acid, tartaric acid, ascorbic acid, malic acid, fumaric acid, succinic acid and malonic acid. Examples of the carbonate include sodium carbonate, sodium bicarbonate, potassium carbonate, potassium bicarbonate, ammonium carbonate and sodium sesquicarbonate, of which the sodium carbonate, sodium bicarbonate and potassium carbonate are particularly preferred.

For the purpose of sufficiently removing the fur coating from the tongue by good bubbling properties, the bubbling component is added in an amount of 15 to 90 wt. % based on the preparation, with 25 to 50 wt. % being particularly preferred.

Examples of the orally-usable medicinal component include halitosis-preventing components, antibacterial agents, anti-inflammatory agents, blood circulation accelerators, fluorine compounds and enzymes. Specific examples of the halitosis-preventing components include copper chlorophyllins sodium, iron chlorophyllins sodium, isopropyl methyl phenol, hinokitiol, licorice, cinnamon, clove, fennel, flavone, champignon extract, basil extract, Oolong tea extract and Hydrangea tea extract, of which the copper chlorophyllins sodium, iron chlorophyllins sodium and combination thereof are more preferred. Examples of the antibacterial agent include cetyl pyridinium chloride, benzalkonium chloride, benzethonium chloride, dequalinium chloride, chlorhexidines and triclosan. Examples of the anti-inflammatory agent include azulene, azulene sulfonic acid salt, glycyrrhetinic acid, lysozyme chloride, Phellodendri cortex extract, Angelicae Radix soft extract and epsilon-aminocaproic acid. Examples of the blood circulation accelerator include tocopherols. Examples of the fluorine compound include sodium monofluorophosphate, potassium monofluorophosphate and sodium fluoride. Examples of the enzyme include dextranase, mutanase, lysozyme, amylase, protease and bacteriolytic enzymes. These components may be used either singly or in combination.

When the halitosis-preventing component is added to the solid preparation of the present invention, fur coating on the tongue, which is said to be a cause for bad breath, is removed by bubbling, followed by adhesion of a large amount of the halitosis-preventing component on the dorsum of tongue, particularly between the filiform papillae. Accordingly, the halitosis-preventing effects show synergistic improvement and these effects last long. Such excellent halitosis-preventing effects in the present invention are particularly preferred.

The amount of the orally-usable medicinal component to be added differs with its kind. From the viewpoint of the drug efficacy or the like, it is added in an amount of 0.001 to 10 wt. % based on the preparation. In particular, it is preferred to add copper chlorophyllins sodium and iron chlorophyllins sodium in amounts of 0.01 to 5 wt. % and 0.001 to 5 wt. %, respectively.

For obtaining synergistic drug efficacy, a ratio of the component (a) to the component (b) falls within a range of 10:1 to 1000:1, with 100:1 to 500:1 being preferred.

As the component (c), excipients ordinarily employed for an orally-usable solid preparation can be used and examples include lactose, starch, dextrins, celluloses, polyethylene glycol, magnesium stearate and maltitol.

The component (c) is added in an amount not greater than 84.999 wt. %, with amounts not greater than 74.999 wt. % being more preferred.

In order to sustain the effects of the orally-usable medicinal component, it is preferred to design the solid preparation of the present invention so as to cause dissolution of the component (a), that is, bubbling earlier than the dissolution of the component (b). In other words., it is desired to control the component ratio of (a):(b) in each part of the solid preparation of the present invention, thereby allowing the bubbling by the component (a) to proceed in the initial stage of the dissolution and allowing the dissolution of the component (b) to proceed even after the completion of the bubbling.

The difference in the occurring time between bubbling and dissolution is derived from the difference in the relative concentration of the component (a) or component (b) in each part of the solid preparation. It is preferred to design the concentration of the component (a) higher in the part where dissolution occurs earlier inside of the cavity and to design the concentration of the component (b) higher in the part where dissolution occurs later.

Figure 2:
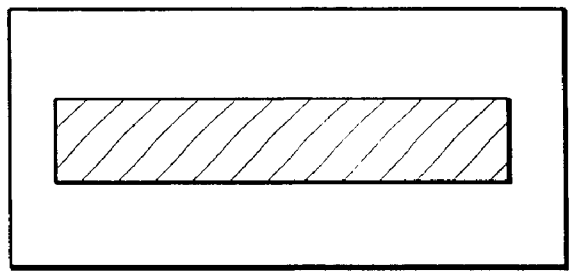
FIG. 2 is a cross-sectional view illustrating a tablet which is formed of an inner layer and an outer layer and is designed to contain the component (a) at a high relative concentration in the outer layer, while containing the component (b) at a high relative concentration in the inner layer, wherein the oblique-line portion shows the part containing the component (b) at a high concentration.
Figure 3:
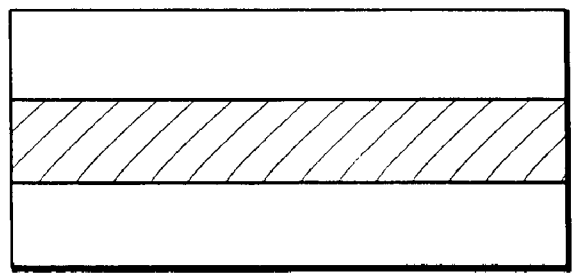
FIG. 3 is a cross-sectional view illustrating a three-layer tablet which is designed to contain the component (b) at a high relative concentration in the intermediate layer, while containing the component (a) at a high relative concentration in each of the upper and lower layers, wherein the oblique portion shows the part containing the component (b) at a high concentration.

Preparations having such a design can be obtained, for example, by the following method: (1) a method to set the relative concentration of the component (a) higher in the outer portion of the solid preparation, while to set that of the component (b) higher in the inner portion (refer to FIG. 1); (2) a method to design the preparation to have an inner layer and outer layer and to set the relative concentration of the component (a) of the outer layer higher, while setting that of the component (b) of the inner layer higher (refer to FIG. 2); or (3) a method to design the preparation to have three stacked layers and to set the relative concentration of the component (b) of the intermediate layer higher, while setting that of the component (a) of each of the upper and lower layers higher (refer to FIG. 3). It should be noted that the relative concentration of the component (a) or that of the component (b) includes the concentration of 0.

To the solid preparation of the present invention, menthol can be added for freshening breath. Menthol may be added uniformly in the preparation or may be added in an amount increased in some part according to the concentration of the component (a) or component (b). In a part containing the component (a) at a higher concentration, menthol can be added in a large amount while alleviating its bitter taste. It is preferred to add menthol in an amount of 0.05 to 5 wt. % based on the preparation. It is more preferred to add menthol in amounts of 0.05 to 1 wt. % and 0.1 to 5 wt. % to a part containing the component (a) at a high relative concentration and to a part containing the component (b) in a high relative concentration, respectively.

To the solid preparation of the present invention, a flavor can be added as needed in order to impart the preparation with a good smell and to improve halitosis-preventing effects. It is particularly preferred to incorporate at least one flavor selected from the group consisting of thyme, celery, cinnamon, sage, pepper, parsley, spearmint, nutmeg, anethole, clove, marjoram, peppermint, basil and rosemary, because addition of such a flavor brings about marked improvement in the halitosis-preventing effects. Such a flavor is preferably added in an amount of 0.001 to 5 wt. %, particularly 0.1 to 2 wt %, To the solid preparation of the present invention, in addition to the above-described components, ordinarily employed ones, for example, lubricants such as sucrose fatty acid ester and fine-particulate silicon dioxide, components satisfying the purpose of the preparation such as vitamins and caffeine, and sweeteners such as saccharin sodium, sucrose, sorbitol, aspartame and erythritol can be added as desired.

Although no particular limitation is imposed on the form of the solid preparation of the present invention, examples include tablets, pills and granules, with tablets being particularly preferred.

The solid preparation of the present invention can be obtained in a conventional manner. A laminated tablet can be obtained by forming a layer containing a bubbling component, forming thereover an orally-usable medicinal component, and then forming thereover a layer containing the bubbling component. A tablet having inner and outer layers can be obtained by forming an inner layer containing an orally-usable medicinal component and then covering it with a layer containing a bubbling component.

For oral hygiene treatment by using the solid preparation of the present invention, it is preferred to take the preparation directly in the mouth without dissolving it in water, bringing it in contact with water in the mouth, thereby causing bubbling and dissolution; and then after dissolution of the preparation, swallowing the solution or discharging it out of the mouth.

The present invention will hereinafter be described in full detail by examples. It should however be borne in mind that the present invention is not limited to or by these examples.

EXAMPLES 1 TO 2, COMPARATIVE EXAMPLES 1 TO 2

Various tablets (1 g, 15 mm in diameter) having the composition as shown in Table 1 were prepared using a hydraulic multi-layer tablet tableting machine produced by Machina Co., Ltd. Breath was collected from each of many subjects in advance in a breathing bag. From those subjects, 40 ones evaluated to have "bad breath" by both of two evaluators (A and B) were selected. They were classified into 4 groups and asked to take the sample shown in Table 1. After the sample was taken, the breath was collected again in a breathing bag and evaluated for studying the effects of each of the tablets. Evaluation was carried out based on the following three standards: ++ for the breath free from halitosis, + for the breath alleviated to some extent in halitosis, and − for the breath not alleviated in halitosis (having halitosis).

As a result, as is apparent from Table 1, the preparations according to the present invention have excellent halitosis-preventing effects compared with the preparation (Comparative Example 1) free of a bubbling component or the preparation (Comparative Example 2) having the bubbling component in an amount less than 15 wt. %.

TABLE 1

| Component (wt. %) | | Example 1 | Example 2 | Comparative Example 1 | Comparative Example 2 |
|---|---|---|---|---|---|
| Corn starch | | 50.32 | 18.32 | 68.32 | 56.32 |
| Sodium bicarbonate | | 9 | 23 | 0 | 6 |
| Ascorbic acid | | 3 | 9 | 0 | 2 |
| Citric acid | | 3 | 9 | 0 | 2 |
| Tartaric acid | | 3 | 9 | 0 | 2 |
| Maltitol | | 30 | 30 | 30 | 30 |
| Saccharin sodium | | 0.5 | 0.5 | 0.5 | 0.5 |
| Sucrose fatty acid ester | | 1 | 1 | 1 | 1 |
| Copper chlorophyllins sodium | | 0.18 | 0.18 | 0.18 | 0.18 |
| Evaluator A | ++ | 5 | 8 | 0 | 1 |
|  | + | 5 | 2 | 3 | 6 |
|  | − | 0 | 0 | 7 | 3 |
| Evaluator B | ++ | 4 | 8 | 0 | 0 |
|  | + | 6 | 2 | 2 | 7 |
|  | − | 0 | 0 | 8 | 3 |

EXAMPLES 3 TO 9

In a similar manner to Example 1, tablets having the composition shown in Table 2, each containing a halitosis-preventing component, were prepared.

TABLE 2

| Component (wt. %) | Example 3 | Example 4 | Example 5 | Example 6 | Example 7 | Example 8 | Example 9 |
|---|---|---|---|---|---|---|---|
| Corn starch | 50.4 | 50.4 | 50.4 | 50.4 | 50.4 | 50.4 | 50.4 |
| Sodium bicarbonate | 9 | 9 | 9 | 9 | 9 | 9 | 9 |
| Ascorbic acid | 3 | 3 | 3 | 3 | 3 | 3 | 3 |
| Citric acid | 3 | 3 | 3 | 3 | 3 | 3 | 3 |
| Tartaric acid | 3 | 3 | 3 | 3 | 3 | 3 | 3 |
| Maltitol | 30 | 30 | 30 | 30 | 30 | 30 | 30 |
| Saccharin sodium | 0.5 | 0.5 | 0.5 | 0.5 | 0.5 | 0.5 | 0.5 |
| Sucrose fatty acid ester | 1 | 1 | 1 | 1 | 1 | 1 | 1 |
| Benzethonium chloride | 0.1 | 0 | 0 | 0 | 0 | 0 | 0 |
| Isopropyl methyl phenol | 0 | 0.1 | 0 | 0 | 0 | 0 | 0 |
| Hinokitiol | 0 | 0 | 0.1 | 0 | 0 | 0 | 0 |
| Clove powder | 0 | 0 | 0 | 0.1 | 0 | 0 | 0 |
| Cinnamon powder | 0 | 0 | 0 | 0 | 0.1 | 0 | 0 |
| Licorice | 0 | 0 | 0 | 0 | 0 | 0.1 | 0 |
| Flavonoids | 0 | 0 | 0 | 0 | 0 | 0 | 0.1 |

EXAMPLE 10

A tablet having the below-described composition was prepared in a similar manner to Example 1. The resulting tablet was excellent in halitosis-preventing and breath freshening effects.

| (Component) | (wt. %) |
|---|---|
| Corn starch | 48.6 |
| Sodium bicarbonate | 9 |
| Ascorbic acid | 3 |
| Citric acid | 3 |
| Tartaric acid | 3 |
| Maltitol | 30 |
| Saccharin sodium | 1.5 |
| Sucrose fatty acid ester | 1 |
| Menthol | 0.8 |
| Flavonoids | 0.1 |

EXAMPLE 11

A tablet having the below-described composition was prepared in a similar manner to Example 1. The resulting tablet was excellent in a halitosis-preventing and breath freshening effects.

| (Component) | (wt. %) |
|---|---|
| Corn starch | 49.52 |
| Sodium bicarbonate | 9 |
| Citric acid | 3 |
| Malic acid | 3 |
| Ascorbic acid | 3 |
| Maltitol | 30 |
| Saccharin sodium | 0.5 |
| Sucrose fatty acid ester | 1 |
| Copper chlorophyllins sodium | 0.12 |
| Iron chlorophyllins sodium | 0.06 |
| Menthol | 0.8 |

EXAMPLE 12

A tablet having the below-described composition was prepared in a similar manner to Example 1. The resulting tablet was excellent in a halitosis-preventing and breath freshening effects.

| (Component) | (wt. %) |
|---|---|
| Corn starch | 43.02 |
| Sodium bicarbonate | 12 |
| Citric acid | 4 |
| Malic acid | 4 |
| Ascorbic acid | 4 |
| Maltitol | 30 |
| Saccharin sodium | 0.5 |
| Sucrose fatty acid ester | 1 |
| Copper chlorophyllins sodium | 0.12 |
| Iron chlorophyllins sodium | 0.06 |
| Menthol | 0.8 |
| Flavor (thyme) | 0.5 |

EXAMPLE 13

Various three-layer tablets (each, 1 g, 15 mm in diameter, weight ratio: outer layer/inner layer/outer layer=1/1/1) having the composition shown in Table 3 were prepared using a hydraulic multi-layer tablet tableting machine produced by Machina Co., Ltd. From 14 persons having a coated tongue, breath was collected in a breathing bag. Those persons were classified into two groups, each group consisting of 7 persons, and were asked to take two kinds of three-layer tablets shown in Table 3. Three hours later, breath was collected in a breathing bag again from them. The presence or absence of bad breath before and after the intake of the three-layer tablet was evaluated by a panel of two experts. Evaluation was carried out based on the following three standards: ⊚ for the breath free from halitosis, ○ for the breath alleviated to some extent in halitosis, and × for the breath not alleviated in halitosis (having halitosis). The results are shown in Table 4.

TABLE 3

| | (wt. %) | | | |
|---|---|---|---|---|
| | Example 13 | | Comparative Example 3 | |
| | Outer layer | Inner layer | Outer layer | Inner layer |
| Corn starch | 50.5 | 68.29 | 68.5 | 68.29 |
| Sodium bicarbonate | 9 | 0 | 0 | 0 |
| Ascorbic acid | 3 | 0 | 0 | 0 |
| Citric acid | 3 | 0 | 0 | 0 |
| Tartaric acid | 3 | 0 | 0 | 0 |
| Maltitol | 30 | 30 | 30 | 30 |
| Saccharin sodium | 0.5 | 0.5 | 0.5 | 0.5 |
| Sucrose fatty acid ester | 1 | 1 | 1 | 1 |
| Copper chlorophyllins sodium | 0 | 0.21 | 0 | 0.21 |

As is apparent from Tables 4 and 5, the preparation according to the present invention obtained by setting a relative concentration of the component (a) high in the part which starts dissolution earlier in the mouth and setting the relative concentration of a component (b) high in the part which starts dissolution later is also excellent in durability of the medicinal component.

TABLE 4

| Expert A | | | Expert B | | |
|---|---|---|---|---|---|
| Evaluation | Example 3 | Comp. Ex. 3 | Evaluation | Example 3 | Comp. Ex. 3 |
| ⊚ | 5 | 0 | ⊚ | 6 | 0 |
| ○ | 2 | 1 | ○ | 1 | 2 |
| X | 0 | 6 | X | 0 | 5 |

EXAMPLE 14

A core-having tablet having a diameter of 15 mm and thickness of 5 mm was prepared using a core-forming rotary tableting machine produced by Kikusui Seisakujo Co., Ltd. First, a tablet of having a diameter of 10 mm and thickness of 3 mm was prepared by a hydraulic tableting machine as a core tablet. The tablet prepared had, as an outer layer, the outer layer of Example 13 and, as a core, the inner layer of Example 13.

Similar to Example 13, from seven subjects having fur coating on the tongue, breath was collected in a breathing bag. Three hours after the use of the core-having tablet, breath was collected again in a breathing bag and a panel of two experts were asked to evaluate the presence or absence of halitosis before and after the use of the tablet. The evaluation was conducted based on the following three standards: ⊚ for the breath free from halitosis, ○ for the breath alleviated to some extent in halitosis and × for the breath not alleviated in halitosis. The results are shown in Table 5.

TABLE 5

| Evaluation | Expert A | Expert B |
|---|---|---|
| ⊙ | 5 | 4 |
| ○ | 2 | 3 |
| × | 0 | 0 |

EXAMPLE 15

Various three-layer tablets (1 g, 15 mm in diameter, weight ratio: outer layer/inner layer/outer layer=1/1/1) containing the medicinal component as shown in Table 6 were prepared in a similar manner to Example 13. As a result, it was found that the tablets were excellent both in halitosis-preventing effects and durability of the effects.

TABLE 6

(wt. %)

| | Outer Layer | Innerlayer 1 | 2 | 3 | 4 | 5 | 6 |
|---|---|---|---|---|---|---|---|
| Corn starch | 50.5 | 68.4 | 68.4 | 68.4 | 68.4 | 68.4 | 68.4 |
| Sodium bicarbonate | 9 | 0 | 0 | 0 | 0 | 0 | 0 |
| Ascorbic acid | 3 | 0 | 0 | 0 | 0 | 0 | 0 |
| Citric acid | 3 | 0 | 0 | 0 | 0 | 0 | 0 |
| Tartaric acid | 3 | 0 | 0 | 0 | 0 | 0 | 0 |
| Maltitol | 30 | 30 | 30 | 30 | 30 | 30 | 30 |
| Saccharin sodium | 0.5 | 0.5 | 0.5 | 05 | 05 | 0.5 | 0.5 |
| Sucrose fatty acid ester | 1 | 1 | 1 | 1 | 1 | 1 | 1 |
| Benzethonium chloride | 0 | 0.1 | 0 | 0 | 0 | 0 | 0 |
| Isopropyl methyl phenol | 0 | 0 | 0.1 | 0 | 0 | 0 | 0 |
| Hinokitiol | 0 | 0 | 0 | 0.1 | 0 | 0 | 0 |
| Clove powder | 0 | 0 | 0 | 0 | 0.1 | 0 | 0 |
| Cinnamon powder | 0 | 0 | 0 | 0 | 0 | 0.1 | 0 |
| Licorice | 0 | 0 | 0 | 0 | 0 | 0 | 0.1 |

EXAMPLE 16

A three-layer tablet (1 g, 15 mm in diameter, weight ratio: outer layer/inner layer/outer layer=1/1/1) containing menthol as shown in Table 7 was prepared in a similar manner to Example 13 and the breath freshening effects of the resulting tablet was evaluated. As a result, it was found that the breath freshening effects and durability of the effects were both excellent when the tablet was used.

TABLE 7

| | Example 16 | |
|---|---|---|
| | Inner layer | Outer layer |
| Corn starch | 48.4 | 67.89 |
| Sodium bicarbonate | 10 | 0 |
| Citric acid | 5 | 0 |
| Malic acid | 5 | 0 |
| Maltitol | 30 | 30 |
| Saccharin sodium | 0.5 | 0.5 |
| Sucrose fatty acid ester | 1 | 1 |
| Copper chlorophyllins sodium | 0 | 0.21 |
| Menthol | 0.1 | 0.4 |

EXAMPLE 17

In a similar manner to Example 13, a three-layer tablet (1 g, 15 mm in diameter, weight ratio: outer layer/inner layer/outer layer=1/1/1) as shown in Table 8 was prepared using copper chlorophyllins sodium and iron chlorophyllins sodium as medicinal components. As a result, it was found that the tablet was excellent both in halitosis-preventing effects and durability of the effects.

TABLE 8

| | Example 17 | |
|---|---|---|
| | Inner layer | Outer layer |
| Corn starch | 48.4 | 67.89 |
| Sodium bicarbonate | 10 | 0 |
| Citric acid | 5 | 0 |
| Malic acid | 5 | 0 |
| Maltitol | 30 | 30 |
| Saccharin sodium | 0.5 | 0.5 |
| Sucrose fatty acid ester | 1 | 1 |
| Copper chlorophyllins sodium | 0 | 0.11 |
| Iron chlorophyllins sodium | 0 | 0.1 |
| Menthol | 0.1 | 0.4 |

EXAMPLE 18

In a similar manner to Example 13, a three-layer tablet (1 g, 15 mm in diameter, weight ratio: outer layer/inner layer/outer layer=1/1/1) as shown in Table 9 was prepared using copper chlorophyllins sodium and iron chlorophyllins sodium as medicinal components. As a result, it was found that the tablet was excellent both in halitosis-preventing effects and durability of the effects.

TABLE 9

| | Example 18 | |
|---|---|---|
| | Inner layer | Outer layer |
| Corn starch | 48.4 | 67.39 |
| Sodium bicarbonate | 10 | 0 |
| Citric acid | 5 | 0 |
| Malic acid | 5 | 0 |
| Maltitol | 30 | 30 |
| Saccharin sodium | 0.5 | 0.5 |
| Sucrose fatty acid ester | 1 | 1 |
| Copper chlorophyllins sodium | 0 | 0.11 |
| Iron chlorophyllins sodium | 0 | 0.1 |
| Menthol | 0.1 | 0.4 |
| Flavor (spearmint) | 0.3 | 0.5 |

TEST 1

With regards to the three-layer tablet obtained in Example 13 and tablets prepared in accordance with the below-described formulations, presence or absence of bad breath was evaluated. As a result, it was found that the tablet obtained in Example 13 was excellent in the halitosis-preventing effects and the durability of the effects.

TABLE 10

| | Non-effervescent monolayer tablet | Effervescent monolayer tablet |
|---|---|---|
| Corn starch | 68.43 | 56.43 |
| Sodium bicarbonate | 0 | 6 |
| Ascorbic acid | 0 | 2 |
| Citric acid | 0 | 2 |
| Tartaric acid | 0 | 2 |

TABLE 10-continued

|  | Non-effervescent monolayer tablet | Effervescent monolayer tablet |
|---|---|---|
| Maltitol | 30 | 30 |
| Saccharin sodium | 0.5 | 0.5 |
| Sucrose fatty acid ester | 1 | 1 |
| Copper chlorophyllins sodium | 0.07 | 0.07 |

What is claimed is:

1. A method of freshening breath comprising:

placing an at least two layered tablets in the mouth, said at least two layers containing the following components:

(A) an effervescent component: 15 to 90 wt %;

(B) an orally usable medicinal component: 0.001 to 10 wt %; and (C) an excipient not greater than 84.99 wt %, wherein a ratio of (A) to (B) ranges from 10:1 to 1000: 1, and wherein the concentration of (A) is higher in an outer layer of said tablet and the concentration of (B) is higher in an inner layer of said tablet.

2. The method of claim 1, wherein by controlling the component ratio of (A):(B) in each part of the solid preparation, the bubbling owing to the component (A) is rendered to proceed in the initial stage of dissolution in the mouth and the dissolution of the component (B) is rendered to proceed even after completion of the bubbling.

3. The method of claim 1, wherein said component (A) contains a carbonate and organic acid.

4. The method of claim 1, wherein component (B) is triclosan.

5. The method of claim 1, wherein said tablet includes peppermint.

6. The method of claim 1, wherein said tablet includes menthol.

7. The method of claim 1, wherein component (B) comprises copper chlorophyllins sodium.

* * * * *

UNITED STATES PATENT AND TRADEMARK OFFICE
CERTIFICATE OF CORRECTION

PATENT NO.    : 6,428,770 B1
DATED         : August 6, 2002
INVENTOR(S)   : Shigeto Kayane et al.

It is certified that error appears in the above-identified patent and that said Letters Patent is hereby corrected as shown below:

<u>Column 9,</u>
Line 54, "Inner layer" should read -- Outer layer --
Line 54, "Outer layer" should read -- Inner layer --

<u>Column 10,</u>
Lines 11 and 37, "Inner layer" should read -- Outer layer --
Lines 11 and 37, "Outer layer" should read -- Inner layer --

Signed and Sealed this

Twelfth Day of August, 2003

JAMES E. ROGAN
*Director of the United States Patent and Trademark Office*